(12) United States Patent
Li

(10) Patent No.: US 11,213,429 B1
(45) Date of Patent: Jan. 4, 2022

(54) DUAL LENS DIMMABLE EYEWEAR

(71) Applicant: Shenzhen Wicue Optoelectronics Co. LTD., Guangdong (CN)

(72) Inventor: Fenghua Li, Shenzhen (CN)

(73) Assignee: SHENZHEN WICUE OPTOELECTRONICS CO. LTD.

(*) Notice: Subject to any disclaimer, the term of this patent is extended or adjusted under 35 U.S.C. 154(b) by 0 days.

(21) Appl. No.: 17/169,007

(22) Filed: Feb. 5, 2021

(51) Int. Cl.
| | |
|---|---|
| G02F 1/1335 | (2006.01) |
| A61F 9/02 | (2006.01) |
| G02F 1/1337 | (2006.01) |
| G02F 1/137 | (2006.01) |
| G02F 1/133 | (2006.01) |

(52) U.S. Cl.
CPC ............ A61F 9/023 (2013.01); G02F 1/1337 (2013.01); G02F 1/13324 (2021.01); G02F 1/13725 (2013.01); G02F 1/133531 (2021.01); A63B 2244/19 (2013.01)

(58) Field of Classification Search
None
See application file for complete search history.

(56) References Cited

U.S. PATENT DOCUMENTS

| | | | |
|---|---|---|---|
| 5,184,156 A | 2/1993 | Black et al. | |
| 2008/0013000 A1* | 1/2008 | Park | A61F 9/023 349/13 |
| 2008/0252801 A1 | 10/2008 | Furuta | |
| 2009/0213283 A1* | 8/2009 | Burlingame | G02F 1/13318 349/14 |
| 2014/0152632 A1 | 6/2014 | Shedletsky et al. | |
| 2017/0068112 A1 | 3/2017 | Bhatta et al. | |
| 2018/0188538 A1 | 7/2018 | Bell | |
| 2018/0321523 A1 | 11/2018 | Robinson et al. | |
| 2019/0068960 A1* | 2/2019 | Jacobs | G02B 26/026 |
| 2019/0391447 A1 | 12/2019 | Kato | |
| 2020/0089025 A1 | 3/2020 | Li | |

FOREIGN PATENT DOCUMENTS

| | | |
|---|---|---|
| CN | 206096661 | 4/2017 |
| EP | 0341519 | 11/1989 |
| EP | 03241674 | 11/2017 |

(Continued)

OTHER PUBLICATIONS

U.S. Office Action dated Jul. 9, 2020 issued in U.S. Appl. No. 16/569,374.

(Continued)

*Primary Examiner* — James A Dudek
(74) *Attorney, Agent, or Firm* — Weaver Austin Villeneuve & Sampson LLP

(57) ABSTRACT

An eyewear apparatus may comprise an inner lens, an outer lens coupled to the inner lens, a liquid crystal film positioned between the inner lens and the outer lens, and a controller connected with the liquid crystal film and configured to provide a voltage to the liquid crystal film. The outer lens has a three-dimensional (3D) curvature characterized by a curvature along a first direction and a curvature along a second direction different from the first direction. The inner lens has a two-dimensional (2D) curvature characterized by a curvature along the first direction and substantially no curvature along the second direction.

11 Claims, 6 Drawing Sheets

(56) References Cited

FOREIGN PATENT DOCUMENTS

GB            2152661        8/1985
WO    WO 2020056251    3/2020

OTHER PUBLICATIONS

Notice of Allowance dated Jan. 27, 2021 issued in U.S. Appl. No. 16/569,374.
PCT International Search Report and Written Opinion dated Jan. 31, 2020 issued in PCT/US2019/051007.
PCT Invitation to Pay Additional Fees, and Where Applicable, Protest Fee dated Dec. 4, 2019 issued in PCT/US2019/051007.

* cited by examiner

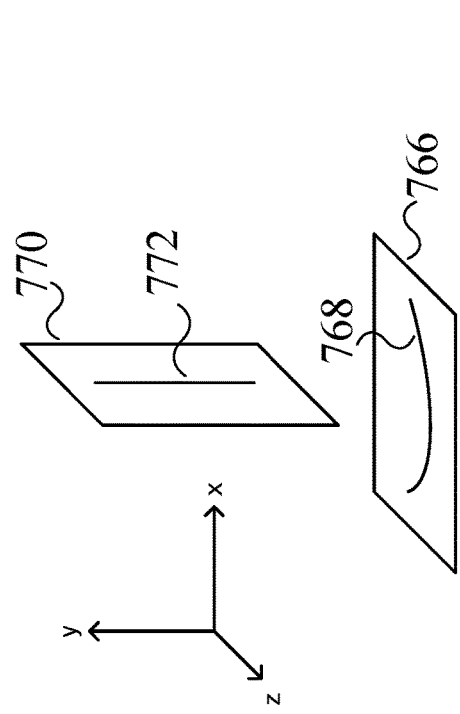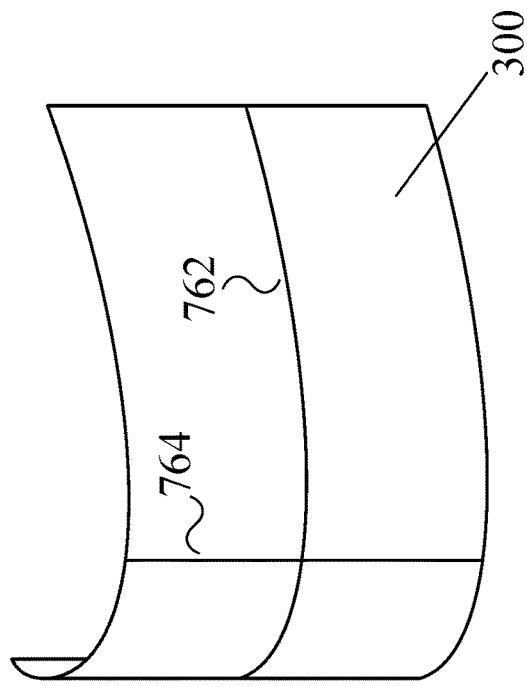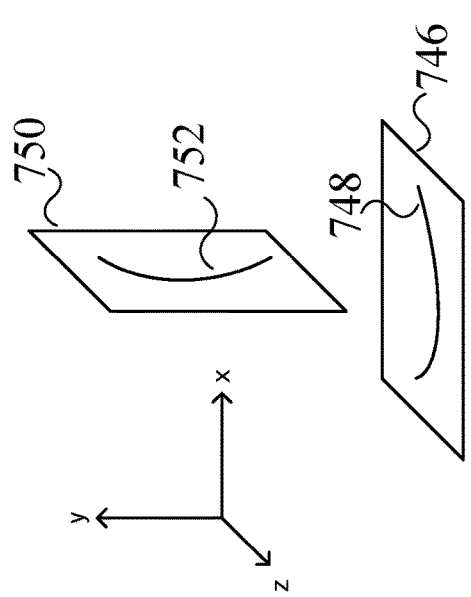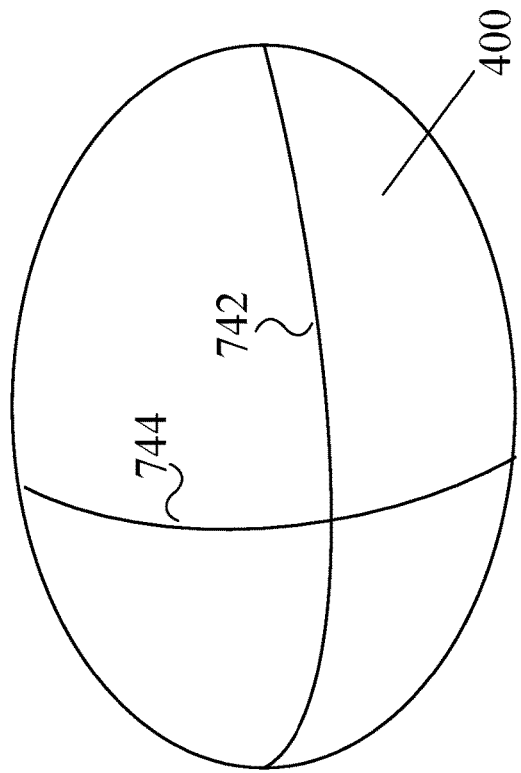
FIG. 7A
FIG. 7B

DUAL LENS DIMMABLE EYEWEAR

BACKGROUND

The present disclosure relates to the technical field of eyewear and specifically to eyewear having an electronically dimmable capability.

Eyewear often serve an important role in protecting a user's eyes from glare, sunlight, and reflections. Examples of eyewear include ski goggles, which are specialized protective spectacles used in icy and snowy environments. They are used as protective equipment for people in skiing, climbing snowy mountains and other sports. They serve not only an aesthetic function, but also to filter light and block the wind. In addition, they can protect the user's eyes from flying debris or impact associated with falling, as well as provide other protective functions.

At present, protective eyewear such as ski goggles are mainly composed of frames and lenses. The lenses used are generally single-layer lenses, which have poor anti-fog eye protection and low impact resistance. Also, when users wear ski goggles for outdoor sports, for example, it is often difficult to avoid encountering strong light, a certain monochromatic light intensity, or a scene environment with frequent light intensity changes. A need exists for eyewear that can provide more effective protection.

BRIEF SUMMARY

The present disclosure an eyewear apparatus, such as electronic dimming ski goggles. The eyewear apparatus may comprise an inner lens, an outer lens coupled to the inner lens, a liquid crystal film positioned between the inner lens and the outer lens, and a controller connected with the liquid crystal film and configured to provide a voltage to the liquid crystal film. The outer lens has a three-dimensional (3D) curvature characterized by a curvature along a first direction and a curvature along a second direction different from the first direction. The inner lens has a two-dimensional (2D) curvature characterized by a curvature along the first direction and substantially no curvature along the second direction.

BRIEF DESCRIPTION OF THE DRAWINGS

Aspects of the disclosure are illustrated by way of example. In the accompanying figures, like reference numbers indicate similar elements.

FIGS. 7A and 7B demonstrate different types of curvature that may be exhibited by the outer lens and inner lens described previously in FIGS. 1, 2, and 5.

DETAILED DESCRIPTION

Figure 1:
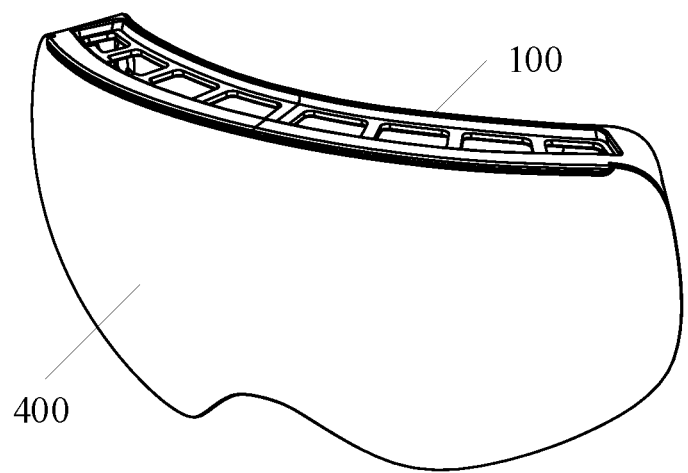
FIG. 1 is a schematic diagram of the structure of an electronic dimming ski goggles in an embodiment of the disclosure.

Several illustrative embodiments will now be described with respect to the accompanying drawings, which form a part hereof. While particular embodiments, in which one or more aspects of the disclosure may be implemented, are described below, other embodiments may be used and various modifications may be made without departing from the scope of the disclosure or the spirit of the appended claims.

The main purpose of the disclosure is to propose a dimmable eyewear apparatus. In one embodiment, the eyewear apparatus comprises electronic dimming ski goggles, which may provide anti-fog eye protection, impact resistance, improved aesthetics and dimming capability. The electronic dimming ski goggles include a frame and lenses arranged on the frame, a control circuit board, and a housing. The housing may be clamped in place. The lenses include an inner lens and an outer lens. The inner lens and the outer lens are arranged at intervals on the inner and outer sides of the lens frame, and the inner lens is connected to a control circuit board. The inner lens may comprise liquid crystal material that is electronically controlled. The lens may be cylindrical in shape, while the outer lens may be spherical in shape.

The electronic dimming ski goggles may further include a solar cell arranged on the frame and electrically connected to the control circuit board.

The liquid crystal lens may include a first polarizer, a first substrate layer, a first conductive layer, a first alignment layer, a liquid crystal layer, a second alignment layer, a second conductive layer, a second substrate layer, and a second polarizer, stacked in sequence. The control circuit board includes a drive circuit electrically connected to the first conductive layer and the second conductive layer, and the absorption axes of the first polarizer and the second polarizer are arranged vertically or parallel, so the liquid crystal layer adopts one of twisted nematic (TN) liquid crystal material, vertical alignment (VA) liquid crystal material, electronically controlled birefringence (ECB) liquid crystal material and super-twisted nematic (STN) liquid crystal material.

Optionally, the liquid crystal lens includes a third substrate layer, a third conductive layer, a third alignment layer, a guest host (GH) liquid crystal layer, a fourth alignment layer, a fourth conductive layer, and a fourth substrate layer stacked in sequence, and the control circuit board includes a driving circuit electrically connected to the third conductive layer and the fourth conductive layer.

The middle part of the upper profile of the frame may be provided with a receiving recess for installing the solar cell and the control circuit board, and a cover plate located on the inner side thereof for covering the receiving recess.

The inner lens may be glued and fixed to the frame by double-sided adhesive tape. The outer lens may be glued and fixed to the lens frame by double-sided adhesive tape, or a lens mounting frame is detachably connected to the lens frame, and the outer lens is located on the lens mounting frame.

The outer peripheral contour of the housing may be configured with a stepped structure, and the stepped structure may include a connecting portion and an enclosing portion that are opposed to the frame.

The upper profile of the housing may be configured with a convex strip, and the outer lens may be provided with a notch adapted to the convex strip.

The electronic dimming ski goggles may further include an elastic band detachably connected with the housing.

The left and right sides of the housing may be respectively provided with fixing components for clamping the elastic band. The fixing components may include a fixing seat and a clamping member. The fixing seat may be provided with a clamping cavity. The inner wall of the holding cavity may be provided with a number of strip-shaped protrusions arranged at intervals in sequence. Adjacent two sides of the fixing seat may be respectively provided with openings for the elastic band to enter and exit the holding cavity and to connect to the holding cavity. A plurality of clamping posts arranged at intervals may be arranged on the clamping member, and the clamping posts may be staggered with the strip-shaped protrusions to clamp the elastic band.

Embodiments of the present disclosure may have the following beneficial effects. The electronic dimming ski goggles includes an inner lens and an outer lens. The inner lens and the outer lens are arranged on the inner and outer sides of the frame at intervals. An air barrier is formed between the inner lens and the outer lens to enhance the interior of the snow goggles. Air circulation can effectively prevent fogging. The setting of double-layer lenses enhances impact resistance and improves anti-fogging eye protection. In addition, the inner lens adopts cylindrical lenses and the outer lens adopts spherical lenses, which enriches the appearance and forms a positive aesthetic effect. In addition, the inner lens comprises a liquid crystal lens, which can be dimmed to adapt to different ambient light, protect user's eyesight, and enhance user experience.

In the following, in conjunction with the drawings in the embodiments of the present disclosure, a clear and complete description of the solutions in the embodiments of the present disclosure will be given. Obviously, the described embodiments are only a part of the embodiments of the present disclosure, rather than all implementations. example. Based on the embodiments of the present disclosure, all other embodiments obtained by those of ordinary skill in the art without creative work shall fall within the protection scope of the present disclosure.

Figure 2:
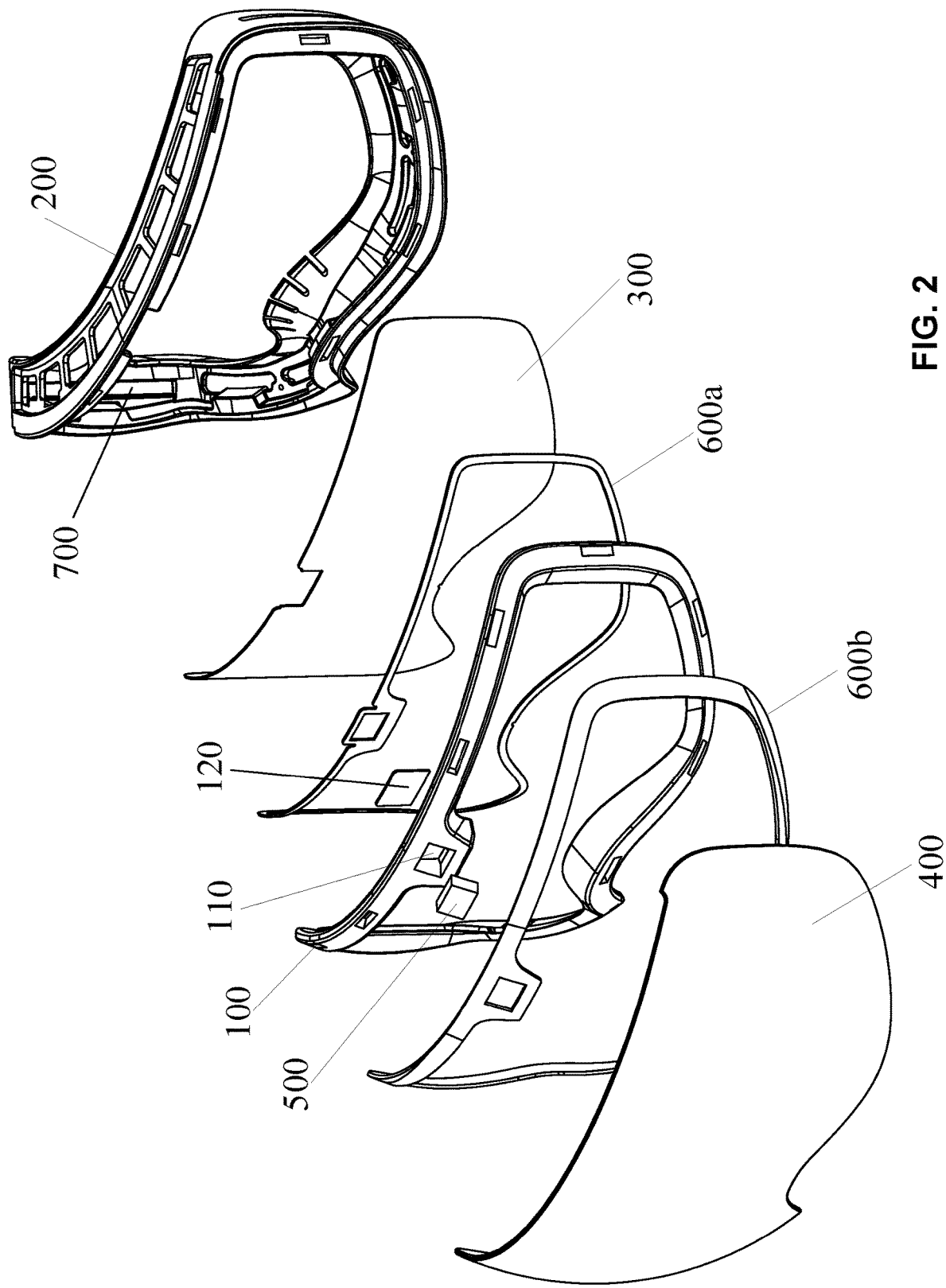
FIG. 2 is an exploded view 1 of the electronic dimming ski goggles in FIG. 1.

With reference to FIGS. 1 and 2, the electronic dimming ski goggles according to an embodiment of the disclosure includes a frame 100 and lenses arranged on the frame 100, a control circuit board, and a housing 200. The frame 100 may also be referred to as a lens frame, spectacle frame, or mirror frame. The housing 200 may also be referred to as a shell sleeve. Here, the housing 200 is clamped on the outer periphery of the frame 100. The lenses include an inner lens 300 and an outer lens 400. The inner lens 300 may also be referred to as an inner layer lens. The outer lens 400 may also be referred to as an outer layer lens. Here, the inner lens 300 and the outer lens 400 are indirectly coupled to one another via the frame 100. The inner lens 300 and the outer lens 400 are spaced apart on the inner and outer sides of the frame 100. The inner lens 300 is electrically connected to the control circuit board. The liquid crystal lens is cylindrical, and the outer lens 400 is spherical. In certain embodiments, the outer lens 400 may have a reflective coating and may be referred to as a snow mirror.

The electronic dimming ski goggles involved in this embodiment are used, for example, as protective equipment for people to wear when skiing or climbing in snowy conditions. Specifically, the electronic dimming ski goggles are mainly composed of a frame 100, lenses, and a housing 200. The frame 100 can be made of thermoplastic elastomer (TPU), thermoplastic polyester elastomer (TPEE), thermoplastic polyamide elastomer (TPAE) and/or other materials. The lens is a double-layer lens, including an inner lens 300 and an outer lens 400. Both the inner lens 300 and the outer lens 400 may be integrally formed. Because the frame 100 has a certain thickness, the inner lens 300 and the outer lens 400 are arranged at intervals. The lens can be fixed in a variety of ways, such as gluing and other techniques. In addition, the housing 200 matches the shape of the frame 100 and is clamped on the outer periphery of the frame 100 for installation and decoration of the frame 100. When the electronic dimming ski goggles are worn, the housing 200 may match the contours of the user's face. In order to improve wearing comfort, the housing 200 is preferably made of soft material, such as foam, rubber, or other easily deformable material.

Furthermore, the inner lens 300 is configured as a liquid crystal lens, which can realize the dimming function of the electronic dimming ski goggles. Among them, the dimming control method can be manual or automatic. For example, a button electrically connected to the control circuit board may be provided on the frame 100, which is manually controlled by operating the button. Automatic control is explained in the subsequent embodiments.

The inner lens 300 and the outer lens 400 of the electronic dimming ski goggles are arranged on the inner and outer sides of the frame 100 at intervals. An air barrier is formed between the inner lens 300 and the outer lens 400 to enhance the interior of the electronic dimming ski goggles. Air circulation can effectively prevent fogging. The setting of double-layer lenses enhances impact resistance and improves anti-fog eye protection. In addition, the inner lens 300 uses cylindrical lenses, and the outer lens 400 uses spherical lenses, which can also enhance the aesthetic appearance of the goggles. In addition, the inner lens comprises a liquid crystal lens, which can be dimmed to adapt to different ambient light, protect the user's vision, and enhance the user experience.

In one embodiment, referring to FIG. 2, the electronic dimming ski goggles further includes a solar cell 500 arranged on the frame 100 and electrically connected to a controller, which may be implemented as a control circuit board. Among them, the solar cell 500 can receive light from the outside with a certain intensity, convert light energy into electrical energy through the photoelectric effect, and output the electrical energy to the control circuit board to control the liquid crystal lens for dimming through the control circuit board. Such dimming effectively counteracts different ambient light to provide improved eye protection. In various embodiments, the solar cell 500 can serve as a control signal, a source of current/power, or both a control signal and a source of current power for the control circuit board and/or the liquid crystal lens.

Figure 3:
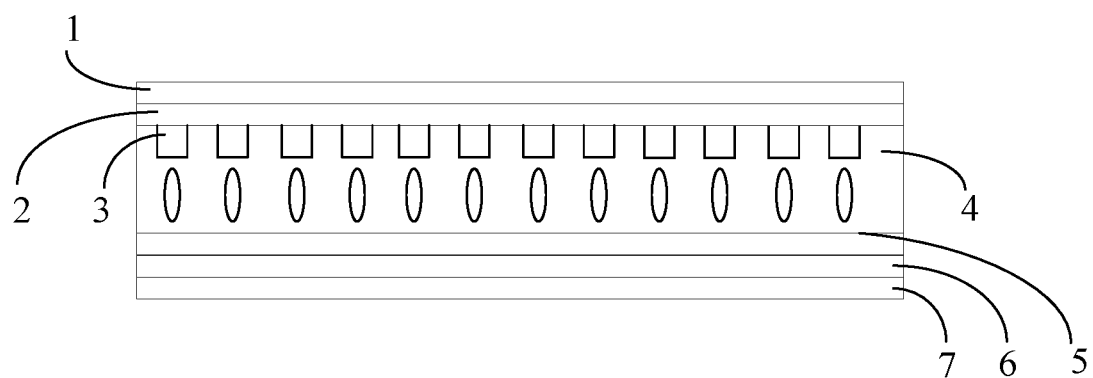
FIG. 3 is a schematic diagram of the structure of the liquid crystal lens of the electronic dimming ski goggles in an embodiment of the disclosure.

In one embodiment, referring to FIG. 3, the liquid crystal lens includes a first polarizer 1, a first substrate layer 2, a first conductive layer 3, a first alignment layer (not shown), a liquid crystal layer 4, and a second alignment layer (not shown) a second conductive layer 5, a second substrate layer 6 and a second polarizer 7, which are arranged in a stack. A control circuit board includes a driving circuit electrically connected to the first conductive layer 3 and the second conductive layer 5. A first absorption axis of the first polarizer 1 and a second absorption axis of the second polarizer 7 may be arranged perpendicularly or parallel to each other. The liquid crystal layer 4 may comprise one of a twisted nematic (TN) liquid crystal material, vertical alignment (VA) liquid crystal material, electrically controlled birefringent (ECB) liquid crystal material or super twisted nematic (STN) liquid crystal material.

In this embodiment, the light source enters the liquid crystal layer 4 and travels according to the arrangement of the liquid crystal molecules, so a natural deflection phenomenon occurs. Therefore, controlling the deflection of the liquid crystal molecules controls the polarization direction of the light. The first substrate layer 2 and the second substrate layer 6 may be made of rigid or flexible material and may include glass, acrylic, and/or other materials. The first conductive layer 3 and the second conductive layer 5 are made of indium tin oxide (ITO) or nano-silver materials. The first alignment layer and the second alignment layer are made of polyimide material, which has microgrooves generated by rubbing to induce the alignment of liquid crystal molecules. The liquid crystal layer 4 may use TN liquid crystal material, VA liquid material, ECB liquid crystal material, STN liquid crystal material, etc. In this embodiment, the liquid crystal layer 4 uses a TN liquid crystal material as an example for description. The TN liquid crystal is a twisted liquid crystal with a twist angle ranging from 90° to 110°, and a typical twist angle is 90°. When an external electric field is not applied to the liquid crystal layer 4, the TN liquid crystal in the liquid crystal layer 4 is in a 90° twisted state and has optical rotation. The light source passes through the first polarizer 1 and then becomes the same as the first polarizer 1. The polarization direction of the polarized light whose absorption axis direction is perpendicular to the TN liquid crystal layer 4 is twisted by 90°, and the polarization direction of the polarized light is rotated by 90°. The polarization direction of the rotated polarized light is the same as the absorption axis direction of the second polarizer 7. It is vertical, so it can pass through the second polarizer 7, and the entire liquid crystal lens is transparent. When a certain intensity of external electric field is applied to the TN liquid crystal layer 4, the long axis direction of the TN liquid crystal will be aligned parallel to the electric field direction, the liquid crystal will no longer have helicity, and the polarization direction of the polarized light passing through the first polarizer 1 will be not be rotated by the liquid crystal. Such unrotated polarized light cannot pass through the second polarizer 7 whose absorption axis is perpendicular to the first polarizer, and the entire liquid crystal lens is dark. In this embodiment, a TN liquid crystal film is used. The TN liquid crystal film has an extremely fast response characteristic, and the response time is usually less than 100 ms, which is much better than the response time of traditional photochromic light glasses, which is easily over 2 minutes. In addition, TN liquid crystal film also has good light-shielding properties, and its light transmittance can reach as low as 0.1%.

Among them, the driving current of the liquid crystal layer 4 is provided by the solar cell 500. When the solar cell 500 receives a certain intensity of light source, it directly converts light energy into electrical energy through the photoelectric effect, that is, generates a direct current (DC) voltage. The drive circuit may operate to convert the DC voltage into an alternating current (AC) voltage, thereby outputting an AC driving voltage of 0-3V to the liquid crystal layer 4 to drive the liquid crystal molecules to rotate so that the long axis direction is parallel to the electric field direction. Regarding the intensity of the unused light source, the DC voltage output by the solar cell 500 is different, so the AC voltage applied to the liquid crystal layer 4 is different, so that the overall liquid crystal lens presents a different light transmittance, so that the liquid crystal dimming glasses can be adjusted according to the ambient light. The function of auto-dimming intensity.

Figure 4:
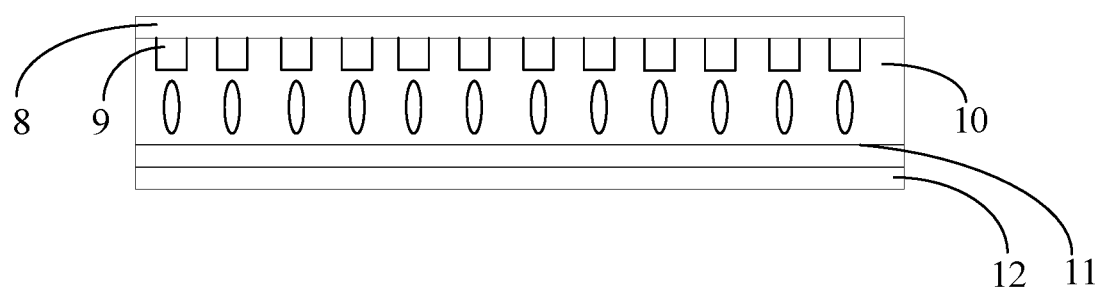
FIG. 4 is a schematic diagram of the structure of the liquid crystal lens of the electronic dimming ski goggles in another embodiment of the disclosure.

In one embodiment, referring to FIG. 4, the liquid crystal lens includes a third substrate layer 8, a third conductive layer 9, a third alignment layer (not shown), a GH liquid crystal layer 10, a fourth alignment layer, and a fourth conductive layer that are sequentially stacked. 11 and the fourth substrate layer 12, the control circuit board includes a driving circuit electrically connected to the third conductive layer 9 and the fourth conductive layer 11. Here, the layers shown in FIG. 4 may constitute additional layers that may be optionally added to the layers shown in FIG. 3.

In this embodiment, the third alignment layer and the fourth alignment layer are made of polyimide material, which has microgrooves generated by rubbing to induce the alignment of liquid crystal molecules. The third substrate layer 8 and the fourth substrate layer 12 are made of smooth insulating transparent materials, such as glass, acrylic materials, etc. The third conductive layer 9 and the fourth conductive layer 11 can be made of indium tin oxide (ITO) or nano-silver materials. The GH liquid crystal layer 10 can a negative guest-host effect liquid crystal.

If the GH liquid crystal layer 10 comprises a negative guest-host effect liquid crystal, when no electric field is applied to the GH liquid crystal layer 10, the long axis of the negative guest-host effect liquid crystal molecules is perpendicular to the third conductive layer 9 and the fourth conductive layer 11, and the liquid crystal molecules react to the incident light. The absorption of the liquid crystal lens is relatively small, so the liquid crystal lens is in a light-transmitting state. When an electric field is applied to the GH liquid crystal layer 10, the negative guest-host effect liquid crystal molecules rotate to a long axis parallel to the third conductive layer 9 and the fourth conductive layer 11. The absorption of incident light is relatively large, so the liquid crystal lens appears dark. In other words, when the GH liquid crystal layer 10 adopts a negative guest-host effect liquid crystal, the driving circuit energizes the third conductive layer 9 and the fourth conductive layer 11, and the liquid crystal lens presents a dark state, and when it is not energized, it presents a light-transmitting state.

In one embodiment, referring to FIG. 2, the middle of the upper profile of the frame 100 is provided with a receiving recess 110 for installing the solar cell 500 and the control circuit board, and a cover located on the inner side thereof for covering the receiving recess board 120. In one implementation, the solar cell 500 is a silicon solar cell 500, which has an appearance size of about 6 mm×8 mm to 10 mm×10 mm and has a high photoelectric conversion efficiency. The size and recess type of the receiving recess 110 are based on the solar cell 500 and the control circuit board. The solar cell 500 is arranged relatively outward in the receiving recess 110, the light source can illuminate the photosensitive surface of the solar cell 500 from the outside of the frame 100. The control circuit board is arranged relatively inward in the receiving recess 110. The outer lens 400 covers the accommodating recess 110 from the outside of the frame 100. In addition, the accommodating recess 110 is covered from the inner side of the frame 100 by the cover plate 120 to prevent the control circuit board from being exposed and prevent the influence of the electronic dimming ski goggles. Overall beautiful.

The stacked structures described in FIGS. 3 and 4 may be implemented as layers of a liquid crystal film. Here, the first substrate layer 2 and the second substrate layer 6, as well as the third substrate layer 8 and the fourth substrate layer 12, can be made of flexible materials. Such materials may comprise, for example, polyethylene terephthalate (PET), polyimide (PI), polypropylene (PP), polyvinyl butyral (PVP), ethylene-vinyl acetate (EVA), polyurethane (TPU), etc. In one embodiment, the inner lens 300 comprises a clear substrate, and the liquid crystal film is attached to the clear substrate. The clear substrate can thus provide mechanical support for the flexible liquid crystal film. For example, the clear substrate can comprise a polycarbonate (PU) material. In one arrangement, the liquid crystal film is attached on the side of the clear substrate opposite the user's face. Thus, the liquid crystal film may be positioned between the inner lens 300 and the outer lens 400. This arrangement can protect the liquid crystal film from wear, scratches, etc., that may otherwise occur over usage and time.

The inner lens 300 mentioned above can realize automatic dimming. In addition, the inner lens 300 can also be designed for manual dimming. Specifically, a rechargeable battery that is electrically connected to the control circuit board is provided on the frame 100. The frame 100 may also house the charging interface and the function keys used to control the liquid crystal lens. The function keys include, for example, an on-off key and a dimming key.

Among them, the inner lens 300 can achieve a light transmittance suitable for human eyes through automatic dimming or manual dimming, thereby achieving the effects of preventing dazzling and glare and protecting eyes.

In one embodiment, referring to FIG. 2, the inner lens 300 is glued and fixed to the frame 100 through a double-sided adhesive tape 600a. The outer lens 400 is glued and fixed to the frame 100 through a double-sided adhesive tape 600b. Alternatively, a lens mounting frame (not shown in the figure) is detachably connected to the frame 100, and the outer lens 400 is attached to the lens mounting frame.

The double-sided adhesive tape 600a and 600b may be arranged along the outline edge of the frame 100. The inner lens 300 and the outer lens 400 are attached to the frame 100 by the double-sided adhesive tape 600a and 600b, respectively, which may be firmly bonded and can ensure the integrity of the electronic dimming ski goggles. The arrangement may provide a pleasing aesthetic. Or, for ease of use, the outer lens 400 can be installed using a lens mounting frame. The outer lens 400 may be attached to the lens mounting frame, and the lens mounting frame can be detachably connected to the frame 100 to realize the arrangement of the outer lens 400. There can be multiple ways of detachable connection, such as magnetic connection, snap connection, etc., which can be selected and set according to actual conditions.

Figure 5:
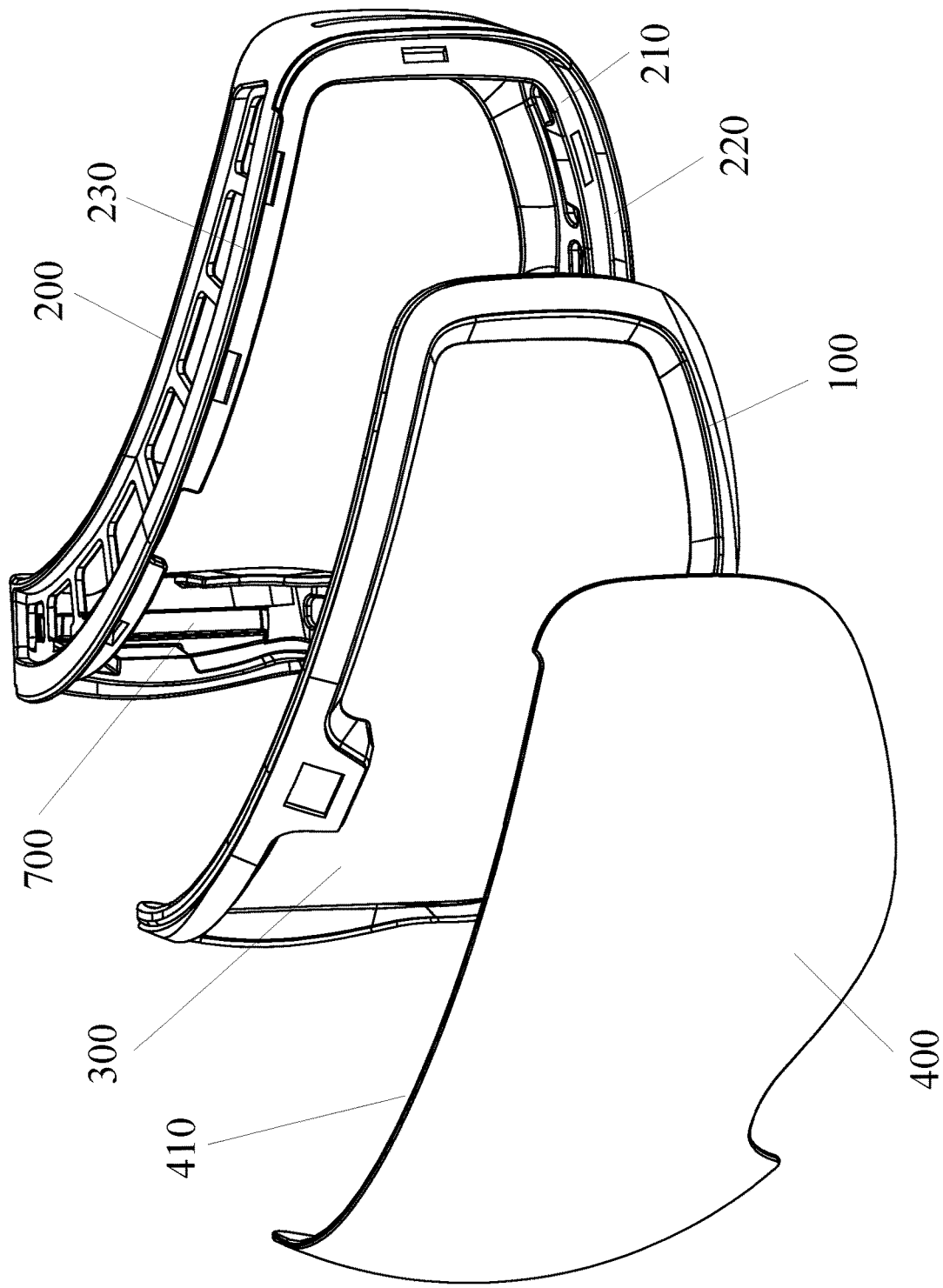
FIG. 5 is the second exploded view, specifically of the outer lens and its manner of assembly and attachment, for the dimming ski goggles in FIG. 1.

In one embodiment, referring to FIG. 5, the outer peripheral contour of the housing 200 is configured with a stepped structure, and the stepped structure includes a connecting portion 210 and an enclosing portion 220 that are opposite to the frame 100. This stepped structure is used to realize the connection between the housing 200 and the frame 100. Specifically, the connecting portion 210 is positively butted with the frame 100, and the enclosing portion 220 is laterally butted with the frame 100 to enclose and hold the frame 100. The design of the structure allows efficient assembly.

Further, referring to FIG. 5, the upper profile of the housing 200 is configured with a convex strip 230, and the outer lens 400 is provided with a notch 410 that matches the convex strip 230. Wherein, the convex strips 230 are arranged along the edge of the upper contour of the housing 200. Correspondingly, the notch 410 of the outer lens 400 is located at the upper edge thereof so as to pass through the notch on the outer lens 400 when the housing 200 and the frame 100 are assembled. The 410 cooperates with the convex strip 230 of the housing 200 to realize rapid positioning and improve assembly efficiency. In addition, the notch 410 provided on the outer lens 400 and the exposure of the convex strips 230 on the housing 200 also enrich the variety of appearances.

In a one embodiment, the electronic dimming ski goggles further includes an elastic band (not shown in the figure) that is detachably connected to the housing 200. That is, the electronic dimming ski goggles can be worn on the human head through use of the elastic band. The elastic band has a certain degree of elasticity and abrasion resistance, which can not only ensure the stability of wearing, but also improve the comfort of wearing. Among them, the elastic band and the housing 200 are detachably connected, which is convenient for replacement.

Figure 6:
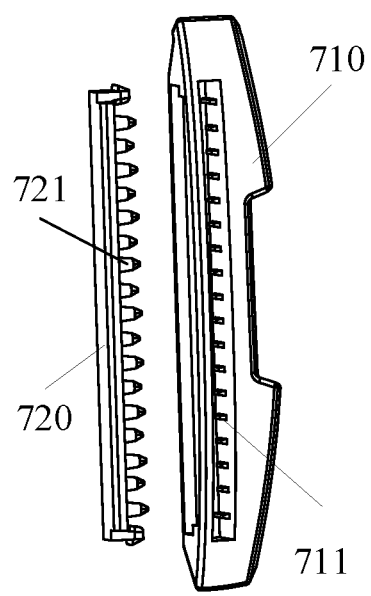
FIG. 6 is a schematic diagram of the structure of the fixing assembly of the electronic dimming ski goggles in an embodiment of the present disclosure.

Further, in order to realize the connection between the elastic band and the housing 200, referring to FIGS. 2, 5 and 6, the left and right sides of the housing 200 are respectively provided with fixing components 700 for holding the elastic band. The fixing components 700 include a fixing seat 710 and The clamping member 720, the fixing seat 710 is provided with a clamping cavity, the inner wall of the clamping cavity is provided with a number of strip-shaped protrusions 711 arranged at intervals in sequence, and the adjacent two sides of the fixing seat 710 are respectively provided with elastic bands. The opening into and out of the clamping cavity and the through hole adapted to the clamping member. The clamping member 720 is provided with a number of clamping posts 721 arranged at intervals in sequence. The clamping posts 721 and the strip-shaped protrusions 711 are staggered to hold the elastic band. The two ends of the elastic band are correspondingly clamped by the fixing components 700 on both sides of the housing 200. The position corresponding to the fixing components 700 on the housing 200 is provided with a gap for the elastic band to pass through, and the elastic band extends from the opening of the fixing seat 710 into the clamping cavity. The clamping member 720 is attached to the fixing seat 710 using the through hole of the fixing seat 710, and the clamping post 721 on the clamping member 720 is interlaced with the strip-shaped protrusion 711 to clamp the elastic band between the two, thereby realize the stable clamping of the elastic band.

FIGS. 7A and 7B demonstrate different types of curvature that may be exhibited by the outer lens and inner lens described previously in FIGS. 1, 2, and 5. FIG. 7A shows an embodiment of the outer lens 400 having a three-dimensional (3D) curvature characterized by a curvature 742 along a first direction and a curvature 744 along a second direction different from the first direction. Here, the first direction may be oriented along an x-axis associated with horizontal direction with respect to a user's face. The second direction may be oriented along a y-axis associated with a vertical direction with respect to the user's face. A z-axis may be associated with a forward gaze direction with respect to the user. The outer lens 400 may intersect a horizontal plane 746, defined by the x-axis and the z-axis, along a first curve 748. The outer lens 400 may also intersect a vertical plane 750, defined by the y-axis and the z-axis, along a second curve 752.

FIG. 7B shows an embodiment of the inner lens 300 having a two-dimensional (2D) curvature characterized by a curvature 762 along the first direction and substantially no curvature 764 along the second direction. Again, the first direction may be oriented along an x-axis associated with horizontal direction with respect to the user's face. The second direction may be oriented along a y-axis associated with a vertical direction with respect to the user's face. A z-axis may be associated with a forward gaze direction with respect to the user. The inner lens 300 may intersect a horizontal plane 766, defined by the x-axis and the z-axis, along a first curve 768. The outer lens 300 may also intersect a vertical plane 770, defined by the y-axis and the z-axis, along a substantially straight line 772.

The above are only part of or preferred embodiments of the disclosure. Neither the text nor the drawings can therefore limit the scope of protection of the disclosure. Any use of the present specification is based on the overall concept of the disclosure. The equivalent structural changes made by the content of the drawings, or direct/indirect application in other related technical fields are all included in the scope of protection of the present disclosure.

What is claimed is:

1. An eyewear apparatus comprising:
   an inner lens;
   an outer lens coupled to the inner lens;
   a liquid crystal film positioned between the inner lens and the outer lens; and
   a controller connected with the liquid crystal film and configured to provide a voltage to the liquid crystal film,
   wherein the outer lens has a three-dimensional (3D) curvature characterized by a curvature along a first direction and a curvature along a second direction different from the first direction, and
   wherein the inner lens has a two-dimensional (2D) curvature characterized by a curvature along the first direction and substantially no curvature along the second direction.

2. The eyewear apparatus according to claim 1, further comprising a solar cell coupled to the controller.

3. The eyewear apparatus according to claim 2,
   wherein the liquid crystal film comprises a first polarizer, a first substrate layer, a first conductive layer, a first alignment layer, a liquid crystal layer, a second alignment layer, a second conductive layer, a second substrate layer and a second polarizer,
   wherein the controller comprises a driving circuit electrically connected to the first conductive layer and the second conductive layer,
   wherein a first absorption axis of the first polarizer and a second absorption axis of the second polarizer are arranged perpendicularly or parallel to each other, and the liquid crystal layer comprises one of a twisted nematic (TN) liquid crystal material, vertical alignment (VA) liquid crystal material, electronically controlled birefringence (ECB) liquid crystal material or super-twisted nematic (STN) liquid crystal material.

4. The eyewear apparatus according to claim 3,
   wherein the liquid crystal film comprises a third substrate layer, a third conductive layer, a third alignment layer, a (guest host) GH liquid crystal layer, and a fourth alignment layer, a fourth conductive layer and a fourth substrate layer stacked in sequence,
   wherein the driving circuit is electrically connected to the third conductive layer and the fourth conductive layer.

5. The eyewear apparatus according to claim 2,
   wherein the eyewear apparatus further comprises a frame positioned between the inner lens and the outer lens, and
   wherein a middle part of an upper profile of the frame is provided with a receiving recess for installing the solar cell and the controller, and
   wherein the eyewear apparatus further comprises a cover plate for covering the receiving recess.

6. The eyewear apparatus according to claim 1,
   wherein the inner lens is attached to the frame by double-sided adhesive tape, and the outer lens is attached to the frame either by (1) double-sided adhesive tape or (2) use of a lens mounting frame, wherein the lens mounting frame is detachably connected to the frame, and the outer lens is attached to the lens mounting frame.

7. The eyewear apparatus according to claim 1, wherein the outer peripheral contour of the housing is configured with a stepped structure, and the stepped structure includes a connecting part and an enclosing part that are opposite to the frame.

8. The eyewear apparatus according to claim 7, wherein the upper profile of the housing is configured with a convex strip, and the outer lens is provided with a notch adapted to the convex strip.

9. The eyewear apparatus according to claim 1, further comprising an elastic band detachably connected to the housing.

10. The eyewear apparatus according to claim 9, wherein:
    a left and a right side of the housing are respectively provided with fixing components for clamping the elastic band,
    the fixing components include a fixing seat and a clamping member,
    the fixing seat is provided with a clamping cavity,
    an inner wall of the clamping cavity is provided with a number of protrusions arranged at intervals in sequence,
    the elastic band enters and exits an opening of the clamping cavity and the through hole that is matched with the clamping member,
    the clamping member is provided with a plurality of clamping posts arranged at intervals in sequence, and
    the clamping posts and the protrusions are staggered to hold the elastic band.

11. The eyewear apparatus according to claim 1, wherein the eyewear apparatus is configured as ski goggles.

* * * * *